(12) United States Patent
Engel

(10) Patent No.: US 6,455,256 B1
(45) Date of Patent: Sep. 24, 2002

(54) METHOD OF AMPLIFYING NUCLEIC ACIDS OF MICROORGANISMS PRESENT IN FRUIT JUICE

(75) Inventor: Stacia R. Engel, Modesto, CA (US)

(73) Assignee: E. & J. Gallo Winery, Modesto, CA (US)

( * ) Notice: Subject to any disclaimer, the term of this patent is extended or adjusted under 35 U.S.C. 154(b) by 0 days.

(21) Appl. No.: 09/710,753

(22) Filed: Nov. 9, 2000

Related U.S. Application Data

(60) Provisional application No. 60/223,229, filed on Aug. 4, 2000.

(51) Int. Cl.[7] .............................. C12Q 1/68; C12P 19/34
(52) U.S. Cl. ........................................... 435/6; 435/91.2
(58) Field of Search ................. 435/6, 91.2; 536/24.33, 536/24.32

(56) References Cited

U.S. PATENT DOCUMENTS 5,556,771 A * 9/1996 Shen et al. ................. 435/91.2

FOREIGN PATENT DOCUMENTS

| JP | 06141899 A | * | 5/1994 |
| JP | 6141899 | | 5/1994 |
| WO | WO-9946405 A1 | * | 9/1999 |

OTHER PUBLICATIONS

DiMichele LJ and Lewis MJ. rapid, species–specific detection of Lactic Acid Bacteria from Beer using the polymerase chain reaction. ASBC Journal, 51(2):63–66, 1993.*

Ogunjimi AA et al. Adsorption of endogenous polyphenols relieves the inhibition by fruit juices and fresh produce of immuno–PCR detection of *Eschrichia coli* 0157:H7. FEMS Immunology and Medical Microbiology, vol. 23:213–220, 1999.*

DiMichele LJ. Rapid, species–specific detection of lactic acid bacteria from beer using the polymerase chain reaction. ASBC Journal, vol. 51(2): 63–66, 1993.*

Stratagene Catalog. Systems and Kits. Stratagene Catalog, p. 132–133, 1995.*

DiMichele et al., "Rapid, Species–Specific Detection of Lactic Acid Bacteria from Beer Using the Polymerase Chain Reaction," *ASBC Journal*, 51(2):63–66 (1993).

Ehrmann et al., "Reverse Dot Blot Hybridization: A Useful Method for the Direct Identification of Lactic Acid Bacteria in Fermented Food," *FEBS Microbiology Letters*, 117:143–149 (1994).

* cited by examiner

*Primary Examiner*—Jeffrey Fredman
*Assistant Examiner*—Prabha Chunduru
(74) *Attorney, Agent, or Firm*—Marshall, Gerstein & Borun.

(57) ABSTRACT

The present invention provides improved real-time methods for amplifying nucleic acids from target microorganisms present in fruit juice comprising the steps of: a) passing fruit juice through a dissolvable filter having a pore size selected to retain the target microorganisms; b) extracting the retentate from the filter with an organic solvent selected to dissolve the filter while not interfering with the integrity of nucleic acids present in the cells of the microorganisms; c) subjecting the extracted to an organic wash step; d) subjecting the extracted retentate to an aqueous wash step; e) concentrating the retentate; and f) subjecting the nucleic acids to an amplification procedure.

34 Claims, No Drawings

METHOD OF AMPLIFYING NUCLEIC ACIDS OF MICROORGANISMS PRESENT IN FRUIT JUICE

This application claims the benefit of U.S. Provisional Patent Application Serial No. 60/223,229, filed Aug. 4, 2000, the disclosure of which is hereby incorporated by reference.

BACKGROUND OF THE INVENTION

The present invention relates generally to methods for identifying microorganisms present in fruit juices generally and more specifically in wine. More specifically, the invention relates to methods of isolating nucleic acids present in fruit juice in order that they may be successfully amplified and/or detected by molecular amplification and detection methods including that known to the art such as polymerase chain reaction (PCR).

The fermentation of grape juice (must) to produce wine is a complex biological process in which yeasts, most typically *Saccharomyces cerevisiae*, are used to convert the sugar content of grape must to ethanol, water, and carbon dioxide. Not only do the many different strains of *Saccharomyces cerevisiae* differ with respect to their metabolic processes and products, but grape must typically comprises a multiplicity of other microorganisms including other fungi, yeasts, and bacteria which react with the grape must during fermentation to produce various metabolic products including aromatic and flavoring compounds. Such products can influence the sensory character of the resulting fermentation product in both positive and negative ways. Conversely, the presence of unwanted microorganisms can lead to undesirable flavors or spoilage. In some cases contaminated must can produce fermentation products characterized by undesirable commercial attributes, affecting flavor, color, and/or mouthfeel. It is thus of intense interest to the vintner to know whether the fermentation is characterized by such microbial contaminants. Similarly, the presence of contaminating microorganisms in the finished wine product is of concern to the wine producer and there exists a desire to ensure the absence of such contaminants. It is also crucial to know if microbes are present after the fermentation has been completed, as the majority of spoilage occurs during the aging and storage of the finished product.

Alternatively, where it is desired to inoculate grape must with a malolactic fermentation bacterium to carry out malolactic fermentation, it is useful to evaluate the growth of the inoculated strain and determine whether the fermentation medium need be reinoculated. Previously, to determine the presence and identity of microorganisms in the grape must, it has been necessary to culture samples of the grape must to "grow up" cell cultures in different selective media. The presence of microbial contaminants can then be identified morphologically or otherwise. Not only is morphological identification sometimes uncertain, but in the case of Dekkera sp., several days are required to culture a sample to determine its presence.

More recently, advances in molecular biology have made it possible to identify microorganisms by amplifying and/or detecting nucleic acid sequences which are uniquely characteristic of those microorganisms by methods such as polymerase chain reaction (PCR), strand displacement amplification (SDA), ligase chain reaction (LCR), RFLPs, direct sequencing (dideoxy method), direct hybridization, and immuno-based assay techniques. In this regard, much recent work has been conducted in the identification of polynucleic acid sequences which are uniquely characteristic of microorganisms present in wine fermentations. For example, ribosomal DNA (rDNA) genes are particularly useful as targets for molecular probes and PCR primers because of their high copy number. Moreover, non-transcribed and transcribed spacer sequences associated with ribosomal genes are usually poorly conserved and thus are useful for the detection and identification of different closely related fungal pathogens. The internal transcribed spacer (ITS) region lies between the 18S and 28S rRNA genes and contains two variable non-coding spacers referred to as ITS1 and ITS2 separated by the 5.85 gene. In addition, the transcriptional units are separated by non-transcribed spacer (NTS) sequences. The ITS and NTS sequences are particularly suitable for the detection of fungal pathogens. PCT International Application WO 99/46405 discloses unique DNA sequences which are useful in the identification of microorganisms involved in fermentations such as *Saccharomyces cerevisiae, Saccharomycodes ludwigii*, Dekkera sp., *Botrytis cinerea*, Penicillium sp., *Hanseniaspora guilliermondii, Debaryomyces carsonii, Pichia anomala, Pichia kluyveri*, and *Candida krusei*. See also Bartowsky, et al., Australian J. of Grape and Wine Research 5:39–44 (1999) which describes the use of PCR for specific detection of the malolactic fermentation bacterium *Oenococcus oeni* (*Leuconostoc oenos*) isolated from bacterial culture.

Despite advances in the molecular identification of microorganisms associated with wine, fruit juice, and fruit-juice fermentations, it has not been possible to successfully conduct a nucleic acid amplification/detection method such as PCR amplification directly on a wine sample. While all the reasons for this remain unclear, they may include concentration effects and may also be related to the presence of potentially inhibitory compounds in the wine, among other factors. It thus remains the case that microorganisms present in wine samples must be subjected to a culturing step in order to provide sufficient quantities of cells to serve as a source of nucleic acids for amplification by PCR or other molecular amplification or detection techniques. The requirement that sample cells be amplified by cell-culturing constitutes a significant limitation to the utility of molecular identification methods because of the time delay (typically several days) inherent in cell-culturing. The vintner is therefore unable to apply real-time adjustments to the fermentation to take advantage of the information provided by the molecular identification techniques. In the case of the presence of undesired microorganisms in a wine fermentation, the loss of time in which to address the outbreak may mean the difference between successfully applying remediation techniques to salvage the fermentation and degradation or ruination of the fermentation batch. Real-time identification of potential microbial problems will enable the proactive, rather than reactive, use of one or more targeted treatments such as cooling, filtering, application of clarification and/or fining agents, anti-microbial substances, and reinoculation, thereby increasing their effectiveness. For this reason, there remains a desire in the art for methods for conducting "real-time" PCR or other amplification techniques not requiring an intermediate cell-culturing step to multiply the cell sample quantity.

While the preceding discussion has focused on the need for improved nucleic acid amplification and/or detection methods for application to the wine industry, it is apparent that there exist similar needs for testing of other fruit juices. Such a need is important in the cider industry but is particularly acute given the growth in popularity of "organic" and other "natural" fruit juices and ciders which are sometimes not subject to pasteurization or treated with preservatives.

Attempts have been made to use conventional cellulosic filters to isolate and concentrate organisms within grape must or wine in order to perform PCR or other amplification or nucleic acid detection techniques on the retentate. Such methods have not been successful and the failure of those methods may relate to the retention of inhibitory compounds within the retentate. More recently, methods such as those of DiMichele and Lewis, *ASBC Journal*, 51:2, 63–66 (1993) have shown promise in conducting real-time PCR for the identification of organisms involved in the fermentation of beer. According to DiMichele and Lewis, *Lactobacillus brevis, L. casei,* and *L. plantarum* were isolated from water and beer by membrane filtration and membrane dissolution using a dissolvable polycarbonate membrane having a pore size of 0.45 micron. Regions of the 16S rRNA sequences unique to each organism were used to generate species-specific PCR products, which were then visualized by gel electrophoresis. The DiMichele reference noted that beer contained a PCR inhibitor that decreased sensitivity.

Despite the promising results reported in beer, the methods of DiMichele et al. would not be expected to work successfully in fruit juices and wine because of differences in the chemical compositions of fruit juices compared with beer. Such differences include the presence of high concentrations of different compounds which can act to interfere with the nucleic acid hybridization and/or chain extension steps required by nucleic acid detection and amplification methods. In particular, it is believed that the acidic pH and high sugar content characteristic of fruit juices may act to interfere with nucleic acid hybridization. Further, the presence of high levels of sediment and particularly the presence of high levels of polyphenolic compounds (e.g. tannins) in juices such as grape juice is suspected to interfere with nucleic acid hybridization and chain extension. Accordingly, there remains a desire in the art for methods by which rapid "real-time" molecular amplification and/or detection methods can be practiced in fruit juices including grape juice and wine samples.

SUMMARY OF THE INVENTION

The present invention relates to the discovery that PCR and other nucleic acid amplification and detection methods can effectively be practiced on nucleic acids derived from the cells of microorganisms isolated from fruit juices generally and particularly from grape juice, wine must, and wine (collectively, referred to herein as "wine") without the necessity of culturing those microorganisms. All varieties of wine may be successfully analyzed according to the method of the invention including white, pink, and red varieties. Specifically, the invention provides a method of isolating cells of target microorganisms present in fruit juice in a form suitable for amplification of the nucleic acids contained therein comprising the steps of: (a) passing fruit juice through a dissolvable filter having a pore size selected to retain said target microorganisms; (b) extracting the retentate from the filter with an organic solvent selected to dissolve said filter while not interfering with the integrity of nucleic acids present in the cells of said test microorganisms; (c) subjecting the extracted cells to an organic wash step; (d) subjecting the extracted cells to an aqueous wash step; and (e) concentrating said cells. In addition, the invention provides alternative methods of (f) isolating nucleic acids from said concentrated cells or (f) subjecting nucleic acids present in the concentrated cells to an amplification and/or detection procedure including those selected from the group consisting of polymerase chain reaction, strand displacement amplification, ligase chain reaction, restriction fragment length polymorphism, dideoxy sequencing, immuno-based sequencing, and hybridization. In some cases, an amplification procedure can be followed by g) detecting the presence of said target nucleic acid sequence. The detection of such target nucleic acids can be carried out by methods well known to the art such as by the use of nucleic acid probes capable of specifically hybridizing with the target nucleic acid sequence. Such probes may be used according to methods well known to the art including, but not limited to, "dip sticks" and other solid phase detection assay devices. The method of the invention is applicable to fruit juices of all sorts but is particularly preferred for use wherein the fruit juice is selected from the group consisting of grape, apple, cranberry, plum, tomato, kiwis, strawberry, raspberry, and citrus juices including lemon, orange, and grapefruit juices. Most preferably the fruit juice is grape juice and is fermented grape juice such as wine or wine must.

The invention also provides kits for isolating cells of microorganisms present in fruit juice (including wine and wine must) in a form suitable for amplification of the nucleic acids contained therein comprising: (a) a dissolvable filter having a pore size of from 0.4 micron to 1 micron with pore sizes of from 0.6 micron to 1 micron being preferred; and (b) an organic solvent selected to dissolve said filter while not interfering with the integrity of nucleic acids present in cells of the target microorganisms. Other kits according to the invention include a kit for amplifying nucleic acids from microorganisms present in fruit juice comprising: (a) a dissolvable filter having a pore size of from 0.4 micron to 1 micron being preferred with pore sizes of from 0.6 micron to 1 micron being preferred; and (b) an oligonucleotide primer selected to specifically hybridize with a polynucleic acid characteristic of a microorganism present in fruit juice. Preferred kits according to the invention further provide: c) a nucleic acid probe capable of hybridizing to the target nucleic acid. Preferred kits according to the invention further include a polyphenolic binding agent which is preferably selected from the group consisting of polyvinypolypyrrolidone and polyvinylpyrrolidone.

DETAILED DESCRIPTION

The present invention provides methods for isolating cells of microorganisms present in fruit juice in a form suitable for amplification and/or detection of nucleic acids contained therein. In this manner, microorganisms present in the fruit juices can be identified by the detection (optionally preceded by amplification) of nucleic acid sequences specific to given microorganisms. As used herein, the term "juice" refers to fermented and unfermented grape and other fruit juices and concentrates and extracts, and is inclusive of those juices and extracts at any stage from and including fresh fruit to a finished fermented wine product. The methods of the present invention have proven useful in isolating microorganisms and amplifying DNA from cells in grapefruit, lemon, and apple juices but are particularly useful when applied to grape must during the fermentation process but are not limited thereto and are also directed to analysis of finished wines.

The methods of the invention involve the step of passing fruit juice through a dissolvable filter characterized by a defined pore size. Such dissolvable (or soluble) filters are dissolvable in organic solvents but retain their structural integrity in aqueous fluids including fruit juices and wine. Polycarbonate filters such as those manufactured by Whatman (Nuclepore®PC) are particularly useful in practice of the invention as they can be dissolved in organic solvents such as chloroform, methylene chloride, and N-methyl-2-pyrrolidone which do not interfere with the integrity of nucleic acids present in the cells of target organisms. By not "interfere with the integrity of nucleic acids," it is meant that an organic solvent which does not alter the structure of polynucleic acids such that they are cleaved or otherwise modified or altered in a way that interferes with nucleic acid hybridization, chain extension, recognition of original poly-acid identity or other molecular techniques used to amplify or detect polynucleic acid sequences.

Other dissolvable filters that can be used according to the invention include mixed cellulose esters (MCE) such as available from Whatman as Membra-Fil® (MF) that are soluble in organic solvents such as acetone, dimethylformamide, dimethylacetamide, N-methyl-2-pyrrolidone, and polyester (PE) filters such as Nuclepore ® (PE) that are soluble in organic solvents which do not interfere with the integrity of nucleic acids such as hexafluoroisopropanol, M-cresol, O-chlorophenol, and phenol/tetrachloroethane (1:1). The dissolvable filters are characterized by a pore size adapted to retain fruit juice and wine-related target microorganisms in order that their DNA may be extracted, amplified, and analyzed. Preferred nominal pore sizes include those greater than 0.4 micron with preferred filters having a pore size from about 0.6 to 1 micron and filters having a nominal pore size of about 0.8 micron being particularly useful in wine analysis because they are capable of retaining live yeasts and other fungi but not bacteria.

Upon filtering of the fruit juice sample through the dissolvable filter and discarding of the filtrate, the retentate present on and within the dissolvable filter material is extracted with an organic solvent selected to dissolve the dissolvable filter while not interfering with the integrity of nucleic acids. While not necessary for practice of the invention, it is also preferred that the organic solvent not unduly damage or lyse the cells of microorganisms retained on the filter. Suitable solvents for use in practice of the invention include N-methyl-2-pyrrolidone, methylene chloride, or chloroform. Further, the organic solvent should be selected such that it does not degrade the DNA contained within the microorganisms in a manner such that it cannot be amplified. While the identity of suitable solvents will be determined by the character of the filter, a preferred solvent for use with polycarbonate filters is a blend comprising phenol, chloroform, and isoamyl alcohol at a ratio of 25:24:1. The extraction is preferably carried out at room temperature and at a pH of about 7.8 because (DNA only, not RNA) nucleic acids will partition into the organic phase at acidic pH (i.e., at acid pH, DNA goes into organic phase, but RNA stays in aqueous). Those of skill in the art will recognize that other blends of these components and of other organic components will serve to dissolve the filter and suitably extract the retained microorganisms in a manner which does not affect the ability to extract and amplify nucleic acid sequences in the microorganisms.

The product of the extraction step comprising the organic solvent, an aqueous solvent (water), dissolved filter, sediment, and extracted microorganisms is then vortexed and centrifuged briefly to separate the aqueous and organic phases. The majority of the extracted cells are present in the aqueous phase which is then transferred to a fresh tube and is subjected to a number of washing steps including one or more wash steps with an organic solvent and one or more wash steps with aqueous and organic solvents to produce a concentrated cell pellet. The organic wash step is preferably carried out with an organic solvent such as phenol or chloroform or mixtures of organic solvents such as a phenol:chloroform:isoamyl alcohol (25:24:1) solution. The aqueous wash step is preferably carried out with deionized water but those of skill in the art will recognize that other aqueous solvents may be used to wash and resuspend the isolated cells and nucleic acids. This cell pellet may then be resuspended according to methods known in the art and the nucleic acids present in the cells used as templates for amplification techniques.

According to one preferred method of the invention, 250 mL of wine is filtered through a 47-mm polycarbonate filter membrane characterized by a pore size of 0.8 micron. The filter containing microorganisms present in the wine is dissolved in a solvent comprising 0.7 mL of deionized water and 1.05 mL of an organic solvent comprising phenol:chloroform:isoamyl alcohol at a ratio of 25:24:1. The product of this extraction comprising sediment, microorganisms, dissolved filter, and solvents is then vortexed and centrifuged briefly to separate aqueous and organic phases. The aqueous phase of the extract is then transferred to a fresh tube and washed with an equal amount of phenol. The product is then mixed and centrifuged briefly to separate organic from aqueous layers. The aqueous phase is then transferred to a fresh tube and washed with an equal amount of phenol:chloroform:isoamyl alcohol (25:24:1). The mixture is then centrifuged briefly to separate layers. The aqueous phase is transferred to a fresh tube and washed with an equal amount of chloroform. The mixture is then centrifuged briefly to separate layers. The aqueous layer is then extracted, and 2.8 mL of deionized water is added and mixed by inversion. The mixture is then centrifuged for five minutes at 5000×g. The liquid is then discharged down to 100 $\mu$L without disturbing the pellet and the pellet is gently resuspended in 2.8 mL of deionized water and the centrifugation step is repeated. The resulting pellet is then resuspended and used as a template in a PCR procedure using 0.4% polyvinylpolypyrrolidone.

The following examples are presented to more clearly illustrate the invention. Examples 1 through 16 are directed to use of conventional filtration methods to isolate microorganism (yeast) cells from wine in preparation for practice of a polymerase chain reaction (PCR) amplification of yeast DNA sequences. Practice of these conventional filtration techniques proved unable to provide sufficient yeast DNA in condition for amplification by PCR despite modification of the basic filtration method of Example 1 by use of surfactants (Examples 2 and 4); adjustment of wine pH (Examples 3 and 4) and use of sonication and shaking methods (Examples 5 through 16). Examples 17 through 19 are directed to use of the method described by DiMichele and Lewis, *ASBC Journal*, 51(2):63–66 (1993) for conducting PCR of yeast DNA in the wine using a dissolvable polycarbonate filter instead of bacteria DNA in beer as taught by DiMchele and Lewis. While there was evidence of weak sporadic but unreproducible amplification when the method was applied to a white wine (Example 17), there was no sign of amplification when applied to pink (Example 18) or red (Example 19) wines. The methods of Examples 17 through 19 differed from that described by DiMichele and Lewis in that the pore size of the polycarbonate filter was 0.8 micron instead of 0.45 micron. Examples 20 and 21 disclose methods according to the present invention including the steps of subjecting the cells extracted from the dissolvable filter to an organic wash step and to an aqueous wash step. The results of these experiments consistently generated weak but reproducible amplification signals for the yeast DNA signals for both the white (Example 20) and red (Example 21) wines. Examples 22 and 23 are directed to a preferred aspect of the invention wherein strong amplification signals were produced for red wines when a polyphenolic binding agent (polyvinylpolypyrrolidone) was incorporated into the PCR buffer.

EXAMPLE 1

Straight Wine

According to this example, amplification of a target nucleotide sequence by PCR was attempted on a straight wine sample without processing according to the methods of the invention. Specifically, amplification by PCR was attempted on artificially-contaminated (i.e., with *Saccharomyces cerevisiae*) or DNA-spiked (*S. cerevisiae*, 100 ng) French Colombard wine using 10 μL as template in 50-μL reactions which contained 5 μL GeneAmp® 10× PCR buffer (PE Applied Biosystems), 0.25 mM each of DATP, dCTP, dGTP, and dTTP (GeneAmp® dNTPs, PE Applied Biosystems), ~25 pM/μL each of forward and reverse primers (ITS5 and ITS4 (White et al., 1990: In PCR Protocols; Eds: Innes et al., pp. 315–322) which are specific to fungal and/or yeast DNA sequences), and 1.25 U AmpliTaq® DNA polymerase (PE Applied Biosystems). Reactions were run on both GeneAmp® PCR Systems 9600 and 9700 (PE Applied Biosystems) through 35 cycles of 30 s at 94° C., 40 s at 54° C., and 2 minutes at 72° C., followed by 10 minutes at 72° C., and proceeded by 10 minutes at 95° C. Samples of each reaction (15 ul) were electrophoresed through 1.2% agarose at 80 V to check for successful amplification, of which there was none.

EXAMPLE 2

Straight Wine Plus Surfactant

According to this example, amplification of a target nucleotide sequence by PCR was attempted on a straight wine sample to which a surfactant had been added because it was believed that a surfactant's emulsifying and stabilizing effects might aid in reducing wine's inhibitory effects on PCR. Amplification was attempted on artificially-contaminated or DNA-spiked (as in Example 1) French Colombard wine using 10 μL as template in 50-μL reactions which contained 1 μL Tween® 80, 5 μL GeneAmp® 10× PCR buffer (PE Applied Biosystems), 0.25 mM each of dATP, dCTP, dGTP, and dTTP (GeneAmp® dNTPs, PE Applied Biosystems), ~25 pM/μL each of forward and reverse primers (as in Example 1), and 1.25 U AmpliTaq® DNA polymerase (PE Applied Biosystems). Reactions were run on thermal cyclers as described in Example 1. Samples of each reaction were electrophoresed as in Example 1 to check for successful amplification, of which there was none.

EXAMPLE 3

Straight Wine, pH Adjusted

According to this example, amplification of a target nucleotide sequence by PCR was attempted on a straight wine sample which had been pH-adjusted because it was believed the acid pH of wine (~3.4) might interfere with PCR. The pH of artificially-contaminated or DNA-spiked (as in Example 1) French Colombard wine was neutralized (pH 7) using NaOH. Amplification by PCR was attempted as in Example 1. Reactions were run on thermal cyclers as described in Example 1. Samples of each reaction were electrophoresed as in Example 1 to check for successful amplification, of which there was none.

EXAMPLE 4

Straight Wine, pH Adjusted Plus Surfactant

According to this example, the acid pH of artificially-contaminated or DNA-spiked (as in Example 1) French Colombard wine was neutralized as in Example 3 and amplification by PCR was attempted as described in Example 2. Reactions were run on thermal cyclers as in Example 1. Samples of each reaction were electrophoresed as in Example 1 to check for successful amplification, of which there was none.

EXAMPLES 5 & 6

Sonication and Shaking I

According to these examples, 250 mL of artificially-contaminated (as in Example 1) French Colombard wine were vacuum-filtered through a mixed cellulose ester membrane (pore size 0.45 micron). Using sterile forceps, the filter was rolled with cell-coated side inward and transferred to a sterile 15-ml centrifuge tube containing 5 ml 100% ethanol (Example 5) or dH$_2$O (Example 6). The tube was sonicated for 5 min, then shaken at 140 strokes/minute for 30 minutes at room temperature. The membrane was removed and discarded, and the remaining ethanol or dH$_2$O was transferred to sterile 1.5-ml tubes and vacuum-centrifuged to complete evaporation. The pellet was resuspended in 230 μL TE (10 mM Tris, 1mM EDTA), of which various amounts (1, 5, and 10 μL) were used as templates for PCR as described in Example 1. Samples of each reaction were electrophoresed as in Example 1 to check for successful, reproducible amplification, of which there was none.

EXAMPLE 7 & 8

Sonication and Shaking II

According to these examples, 250 mL of artificially-contaminated (as in Example 1) French Colombard wine were vacuum-filtered as in Examples 5 & 6. Using sterile forceps, the filter was rolled with cell-coated side inward and transferred to a sterile 15-ml centrifuge tube containing 5 ml 100% ethanol (Example 7) or dH$_2$O (Example 8). The tube was sonicated and shaken as described in Examples 5 & 6. The membrane was removed and discarded, and various amounts of the remaining fluid (1, 5, and 10 ul) were used as templates for PCR as described in Example 1. Samples of each reaction were electrophoresed as in Example 1 to check for successful amplification, of which there was none.

EXAMPLES 9 & 10

Sonication and Shaking III

According to these examples, 250 mL of artificially-contaminated (as in Example 1) Cabernet Sauvignon wine were vacuum-filtered as described in Examples 5 & 6. Using sterile forceps, the filter was transferred cell-side down to a sterile 150-ml beaker containing 5 ml 100% ethanol (Example 9) or dH$_2$O (Example 10). The beaker with filter was sonicated and shaken as in Examples 5 & 6. The membrane was removed and discarded, and the remaining ethanol or dH$_2$O transferred to fresh tubes and vacuum-centrifuged as in Examples 5 & 6. The pellet was resuspended in 230 μL TE, of which various amounts (0.01 [1 μL of 1/100 dilution], 0.1 [1 μL of 1/10 dilution], 1, 5, and 10 μL) were used as templates for PCR as described in Example 1. Samples of each reaction were electrophoresed as in Example 1 to check for successful amplification. No successful, reproducible amplification was obtained.

EXAMPLES 11 & 12

Sonication and Shaking IV

According to these examples, 250 mL of artificially-contaminated (as in Example 1) Cabernet Sauvignon wine were vacuum-filtered as in Examples 5 & 6. Using sterile forceps, the filter was transferred cell-side down to a sterile 150-ml beaker containing 5 ml 100% ethanol (Example 11) or dH$_2$O (Example 12). The beaker with filter was sonicated and shaken as in Examples 5 & 6. The membrane was removed and discarded, and various amounts of the remaining fluid (1, 5, and 10 μL) were used as templates for PCR as described in Example 1. Samples of each reaction were electrophoresed as in Example 1 to check for successful amplification. No successful, reproducible amplification was obtained.

EXAMPLE 13

Sonication and Shaking V

According to this example, 250 mL of artificially-contaminated (i.e., with *Zygosaccharomyces bailii*) White Zinfandel wine were vacuum-filtered as in Examples 5 & 6. Using sterile forceps, the filter was transferred cell-side down to a sterile 150-ml beaker containing 5 ml dH$_2$O. The beaker with filter was sonicated and shaken as in Examples 5 & 6. The membrane was removed and discarded, and various amounts of the remaining fluid (1, 5, and 10 μL) were used as templates for PCR as described in Example 1. Samples of each reaction were electrophoresed as in Example 1 to check for successful amplification. No successful, reproducible amplification was obtained.

EXAMPLES 14 & 15

Sonication and Shaking VI

According to these examples, 250 mL of artificially-contaminated (as in Example 13) White Zinfandel wine were vacuum-filtered as in Examples 5 & 6. Using sterile forceps, the filter was transferred cell-side up (Example 14) or cell-side down (Example 15) to a sterile 47-mm Petri plate containing 5 ml dH$_2$O. The plate with filter was sonicated and shaken as in Examples 5 & 6. The membrane was removed and discarded, and various amounts of the remaining fluid (1, 5, and 10 μL) were used as templates for PCR as described in Example 1. Samples of each reaction were electrophoresed as in Example 1 to check for successful amplification. No successful, reproducible amplification was obtained.

EXAMPLE 16

Sonication and Shaking VII

According to this example, 250 mL of artificially-contaminated (as in Example 1) Chardonnay wine were vacuum-filtered as in Examples 5 & 6. Using sterile forceps, the filter was transferred cell-side up to a sterile 47-mm Petri plate containing 5 ml dH$_2$O. The plate with filter was sonicated and shaken as in Examples 5 & 6. The membrane was removed and discarded, and various amounts of the remaining fluid (1, 5, and 10 μL) were used as templates for PCR as described in Example 1. Samples of each reaction were electrophoresed as in Example 1 to check for successful amplification, of which there was none.

EXAMPLES 17, 18, & 19

Membrane Dissolution I

According to these examples, 250 mL of French Colombard (Example 17—artificially-contaminated as in Example 1), Cabernet Sauvignon (Example 18—artificially-contaminated as in Example 1), and White Zinfandel (Example 19—artificially-contaminated with *Zygosaccharomyces bailii* as in Example 13) wine were vacuum-filtered through a 47-mm polycarbonate membrane (pore size 0.8 micron) Nuclepore® Whatman. The membrane was processed as in DiMichele and Lewis, *ASBC Journal*, 51(2):63–66 (1993), except that reagent volumes were increased by 3.5 times to accommodate the larger filter diameter. Using sterile forceps, the filter was transferred to a sterile 2-ml centrifuge tube, to which 0.7 mL dH$_2$O and 1.05 mL chloroform:isoamyl alcohol (24:1) were added. The tube was vortexed to mix the organic and aqueous phases, and to dissolve the membrane. The tube was then centrifuged briefly to separate the organic and aqueous phases, and the aqueous phase was transferred to a fresh tube. A 2.8-ml portion of water was added, and the tube vortexed to mix, then centrifuged for 5 minutes at 5000×g. The supernatant was removed down to 100 μL and discarded, taking care not to disturb the pellet. The pellet was gently resuspended in 2.8 ml water, and centrifuged for 5 minutes at 5000×g. The supernatant was removed down to 100 μL and discarded. The pellet was gently resuspended in the remaining liquid and various amounts (1, 5, and 10 μL) and dilutions (1 μL each of 1/5 and 1/10) used as template in PCR as described in Example 1. Samples of each reaction were electrophoresed as in Example 1 to check for amplification. Weak nucleic acid amplification occurred sporadically but was not reproducible in white wine (Example 17) and could not be detected at all in red (Example 18) or pink (Example 19) wines.

EXAMPLES 20 & 21

Membrane Dissolution II

According to these examples of practice of the method of the invention, both organic and aqueous wash steps were used to isolate yeast cells for nucleic acid analysis. Specifically, 250 mL of artificially-contaminated (as in Example 1) Malvasia (Example 20) or Zinfandel (Example 21) wine were vacuum-filtered through a 47-mm polycarbonate membrane (pore size 0.8 micron). Using sterile forceps, the filter was transferred to a sterile 2-ml centrifuge tube, to which 0.7 mL dH$_2$O and 1.05 mL phenol:chloroform:isoamyl alcohol (25:24:1) were added. The tube was vortexed to mix the organic and aqueous phases, and to dissolve the membrane. The tube was then centrifuged briefly to separate the organic and aqueous phases, and the aqueous phase was transferred to a fresh tube. An equal amount of phenol was added and the tube was shaken to mix, then centrifuged briefly to separate the organic and aqueous phases. The aqueous phase was transferred to a fresh tube, and an equal amount of phenol:chloroform:isoamyl alcohol (25:24:1) was added. The tube was shaken to mix, then centrifuged briefly to separate the organic and aqueous phases. The aqueous phase was transferred to a fresh tube, and an equal amount of chloroform was added. The tube was shaken to mix, then centrifuged briefly to separate the organic and aqueous phases. The aqueous phase was transferred to a fresh tube, 2.8 ml water was added, and the contents were mixed by inversion. The tube was centrifuged for 5 minutes at 5000×g. The supernatant was removed down to 100 μL and discarded, taking care not to disturb the pellet. The pellet was gently resuspended in 2.8 ml water, and centrifuged for 5 minutes at 5000×g. The supernatant was removed down to 100 μL and discarded. The pellet was gently resuspended in the remaining liquid and various amounts (1, 5, and 10 μL) and dilutions (1 μL each of 1/5 and 1/10) used as template in PCR as described in Example 1. Samples of each reaction were electrophoresed as in Example 1 to check for amplification. Both white (Example 20) and red (Example 21) wines consistently generated weak but reproducible amplification products.

EXAMPLES 22 & 23

Membrane Dissolution III

According to this example, a polyphenolic binding compound (polyvinylpolypyrrolidone) was used to reduce the interference of polyphenolics present in wine with the PCR amplification. Specifically, 250 mL of naturally spoiled Cabernet Sauvignon wine (Example 22) or Cabernet Sauvignon wine artificially-contaminated as in Example 1(Example 23) were vacuum-filtered through a 47-mm polycarbonate membrane (pore size 0.8 micron). Using sterile forceps, the filter was transferred to a sterile 2-ml centrifuge tube, to which 0.7 mL $dH_2O$ and 1.05 mL phenol:chloroform:isoamyl alcohol (25:24:1) were added. The tube was vortexed to mix the organic and aqueous phases, and to dissolve the membrane. The tube was then centrifuged briefly to separate the organic and aqueous phases, and the aqueous phase was transferred to a fresh tube. An equal amount of phenol was added and the tube was shaken to mix, then centrifuged briefly to separate the organic and aqueous phases. The aqueous phase was transferred to a fresh tube, and an equal amount of phenol:chloroform:isoamyl alcohol (25:24:1) was added. The tube was shaken to mix, then centrifuged briefly to separate the organic and aqueous phases. The aqueous phase was transferred to a fresh tube, and an equal amount of chloroform was added. The tube was shaken to mix, then centrifuged briefly to separate the organic and aqueous phases. The aqueous phase was transferred to a fresh tube, 2.8 ml water was added, and the contents were mixed by inversion. The tube was centrifuged for 5 minutes at 5000×g. The supernatant was removed down to 100 µL and discarded, taking care not to disturb the pellet. The pellet was gently resuspended in 2.8 ml water, and centrifuged for 5 minutes at 5000×g. The supernatant was removed down to 100 µL and discarded. The pellet was gently resuspended in the remaining liquid and various amounts (1, 5, and 10 µL) and dilutions (1 µL each of 1/5 and 1/10) used as template in PCR as described in Example 1, except containing 0.4% polyvinylpolypyrrolidone. Samples of each reaction were electrophoresed as in Example 1 to check for amplification. The reactions successfully generated strong amplification products in a consistent and reproducible manner for both the naturally and artificially spoiled red wines and will generate strong amplification products in white and pink wines as well.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of amplifying nucleic acids from a target microorganism present in fruit juice comprising the steps of:
   a) carrying out a microorganism concentration step comprising passing said fruit juice through a dissolvable filter having a pore size selected to retain said target microorganisms;
   b) immediately following said concentration step with the step of extracting the retentate from the filter with an organic solvent selected to dissolve said filter while not interfering with the integrity of nucleic acids present in the cells of said microorganisms;
   c) subjecting the extracted retentate to an organic wash step;
   d) subjecting the extracted retentate to an aqueous wash step;
   e) concentrating said retentate; and
   f) subjecting nucleic acids present in said concentrated retentate to an amplification procedure or a detection procedure.

2. The method of claim 1 wherein the fruit juice is selected from the group consisting of grape, apple, cranberry, citrus, plum, and tomato juices.

3. The method of claim 1 wherein the fruit juice is grape juice.

4. The method of claim 1 wherein the fruit juice is fermenting.

5. The method of claim 1 wherein the fruit juice is wine.

6. The method of claim 1 wherein the amplification or detection procedure is carried out in the presence of a polyphenolic binding agent.

7. The method of claim 6 wherein said polyphenolic binding agent is selected from the group consisting of polyvinylpolypyrrolidone and polyvinylpyrrolidone.

8. The method of claim 1 wherein the nucleic acid amplification or detection procedure is selected from the group consisting of polymerase chain reaction, strand displacement amplification, ligase chain reaction, restriction fragment length polymorphism, dideoxy sequencing, hybridization, and immuno-based sequencing.

9. The method of claim 1 wherein said organic filter is dissolved without lysing said target microorganisms.

10. The method of claim 1 wherein said target microorganism is a yeast.

11. The method of claim 1 wherein said dissolvable filter is a polycarbonate filter.

12. The method of claim 1 wherein said dissolvable filter has a pore size of from 0.4 to 1 micron.

13. A method of isolating nucleic acids from target microorganisms present in fruit juice comprising the steps of:
   a) carrying out a microorganism concentration step comprising passing said fruit juice through a dissolvable filter having a pore size selected to retain said target microorganisms;
   b) immediately following said concentration step with the step of extracting the retentate from the filter with an organic solvent selected to dissolve said filter while not interfering with the integrity of nucleic acids present in the cells of said microorganisms;
   c) subjecting the extracted retentate to an organic wash step;
   d) subjecting the extracted retentate to an aqueous wash step;
   e) concentrating said retentate; and
   f) isolating nucleic acids from said concentrated retentate.

14. The method of claim 13 wherein the fruit juice is selected from the group consisting of grape, apple, cranberry, citrus, plum, and tomato juices.

15. The method of claim 13 wherein the fruit juice is grape juice.

16. The method of claim 13 wherein the fruit juice is fermenting.

17. The method of claim 13 wherein the fruit juice is wine.

18. A method of isolating cells of target microorganisms present in fruit juice in a form suitable for amplification of the nucleic acids contained therein comprising the steps of:
   a) carrying out a microorganism concentration step comprising passing said fruit juice through a dissolvable filter having a pore size selected to retain said target microorganisms;
   b) immediately following said concentration step with the step of extracting the retentate from the filter with an organic solvent selected to dissolve said filter while not interfering with the integrity of nucleic acids present in the cells of said microorganisms;
   c) subjecting the extracted retentate to an organic wash step;
   d) subjecting the extracted retentate to an aqueous wash step; and
   e) concentrating said retentate.

19. The method of claim 18 wherein the fruit juice is selected from the group consisting of grape, apple, cranberry, citrus, plum, and tomato juices.

20. The method of claim 18 wherein the fruit juice is grape juice.

21. The method of claim 18 wherein the fruit juice is fermenting.

22. The method of claim 18 wherein the fruit juice is wine.

23. A method of detecting the presence of a target nucleic acid sequence in microorganisms present in fruit juice comprising the steps of:
   a) carrying out a microorganism concentration step comprising passing said fruit juice through a dissolvable filter having a pore size selected to retain said target microorganisms;
   b) immediately following said concentration step with the step of extracting the retentate from the filter with an organic solvent selected to dissolve said filter while not interfering with the integrity of nucleic acids present in the cells of said microorganisms;
   c) subjecting the extracted retentate to an organic wash step;
   d) subjecting the extracted retentate to an aqueous wash step;
   e) concentrating said retentate;
   f) subjecting nucleic acids present in said concentrated retentate to an amplification procedure; and
   g) detecting the presence of said target nucleic acid sequence.

24. The method of claim 23 wherein presence of said target nucleic acid sequence is detected by hybridization.

25. The method of claim 23 wherein the fruit juice is selected from the group consisting of grape, apple, cranberry, citrus, plum, and tomato juices.

26. The method of claim 23 wherein the fruit juice is grape juice.

27. The method of claim 23 wherein the fruit juice is fermenting.

28. The method of claim 23 wherein the fruit juice is wine.

29. A kit for isolating cells of target microorganisms present in fruit juice in a form suitable for amplification of the nucleic acids contained therein comprising:
   a) a dissolvable filter having a pore size of from 0.4 micron to 1 micron; and
   b) an organic solvent selected to dissolve said filter while not interfering with the integrity of nucleic acids present in cells of target microorganisms; and
   c) a polyphenolic binding agent.

30. The kit of claim 29 wherein said polyphenolic binding agent is selected from the group consisting of polyvinylpolypyrrolidone and polyvinylpyrrolidone.

31. A kit for amplifying nucleic acids from microorganisms present in fruit juice comprising:
   a) a dissolvable filter having a pore size of from 0.4 micron to 1 micron; and
   b) an oligonucleotide primer selected to specifically hybridize with a polynucleic acid characteristic of a microorganism present in fruit juice.

32. The kit of 31 further comprising:
   c) a nucleic acid probe capable of hybridizing to the target nucleic acid.

33. The kit of claim 31 further comprising:
   d) a polyphenolic binding agent.

34. The kit of claim 34 wherein said polyphenolic binding agent is selected from the group consisting of polyvinylpolypyrrolidone and polyvinylpyrrolidone.

* * * * *